United States Patent [19]

Fuchs et al.

[11] 4,350,640
[45] Sep. 21, 1982

[54] PREPARATION OF SUBSTITUTED (CYCLO)ALKANECARBOXYLIC ACID α-CYANO-3-PHENOXY-BENZYL ESTERS

[75] Inventors: Rainer Fuchs; Fritz Maurer, both of Wuppertal; Uwe Priesnitz, Unna-Massen; Hans-Jochem Riebel, Wuppertal, all of Fed. Rep. of Germany

[73] Assignee: Bayer Aktiengesellschaft, Leverkusen, Fed. Rep. of Germany

[21] Appl. No.: 173,545

[22] Filed: Jul. 30, 1980

[30] Foreign Application Priority Data

Aug. 18, 1979 [DE] Fed. Rep. of Germany ....... 2933496

[51] Int. Cl.³ .......................................... C07C 120/00
[52] U.S. Cl. ............................................. 260/465 D
[58] Field of Search ................................. 260/465 D

[56] References Cited

U.S. PATENT DOCUMENTS

| | | | |
|---|---|---|---|
| 3,835,176 | 9/1974 | Matsuo et al. | 260/465 D |
| 4,110,360 | 8/1978 | Sheldon et al. | 260/465 D |
| 4,123,451 | 10/1978 | Sheldon et al. | 260/465 D |

*Primary Examiner*—Dolph H. Torrence
*Attorney, Agent, or Firm*—Sprung, Horn, Kramer & Woods

[57] ABSTRACT

A process for the preparation of a substituted (cyclo) alkanecarboxylic acid α-cyano-3-phenoxy-benzyl ester of the formula

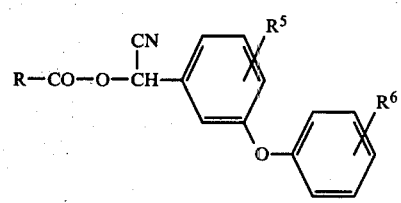

in which R is alkyl or cycloalkyl optionally substituted by halogen, alkyl, cycloalkyl, alkenyl (which is optionally substituted by halogen and/or alkoxy), styryl (which is optionally substituted by halogen, and/or optionally halogen-substituted alkyl, alkoxy, alkylenedioxy and alkylthio radicals), spirocyclically linked, optionally halogen-substituted cycloalk(en)yl (which is optionally benzo-fused) or optionally substituted phenyl and $R^5$ and $R^6$ each independently is hydrogen or halogen, comprising adding an aqueous solution or suspension of at least an equimolar amount of a water-soluble cyanide to a mixture of an alkanecarboxylic acid chloride of the formula

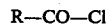

and a 3-phenoxy-benzaldehyde of the formula

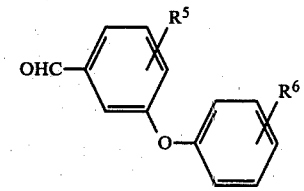

in a hydrocarbon solvent which is virtually immiscible with water at a temperature between about 0° and 80° C.

11 Claims, No Drawings

PREPARATION OF SUBSTITUTED (CYCLO)ALKANECARBOXYLIC ACID α-CYANO-3-PHENOXY-BENZYL ESTERS

The invention relates to an unobvious process for the preparation of certain known substituted (cyclo)alkanecarboxylic acid α-cyano-3-phenoxy-benzyl esters which can be used as agents for combating pests.

It is known that (cyclo)alkanecarboxylic acid α-cyano-3-phenoxy-4-fluoro-benzyl esters, for example 3-(2,2-dichloro-vinyl)- or 3-(2-chloro-2-(4-chloro-phenyl)-vinyl)-2,2-dimethyl-cyclopropane-1-carboxylic acid α-cyano-3-phenoxy-4-fluoro-benzyl ester or α-isopropyl-α-(4-chlorophenyl)-acetic acid α-cyano-3-phenoxy-4-fluoro-benzyl ester, are obtained when the corresponding acid chlorides, for example 3-(2,2-dichloro-vinyl)- or 3-(2-chloro-2-(4-chloro-phenyl)-vinyl)-2,2-dimethyl-cyclopropane-1-carboxylic acid chloride or α-isopropyl-α-(4-chloro-phenyl)-acetic acid chloride, are reacted with α-cyano-3-phenoxy-4-fluoro-benzyl alcohol (see DE-OS's (German Published No.) 2,709,264 and 2,730,515).

However, the yield and quality of the products from this preparative process are unsatisfactory. The main cause of this is probably that the α-cyano-3-phenoxy-4-fluoro-benzyl alcohol employed as the starting compound dissociates very readily into the starting components 3-phenoxy-4-fluoro-benzaldehyde and hydrogen cyanide and virtually cannot be prepared in the pure form.

It is also known that substituted cyclopropanecarboxylic acid α-cyano-benzyl esters are obtained when substituted cyclopropanecarboxylic acid halides are reacted with substituted benzaldehydes in the presence of aqueous solutions of sodium cyanide or potassium cyanide (see DE-OS (German Published No.) 2,231,312 and U.S. Pat. No. 3,835,176). However, α-cyano-benzyl esters are likewise obtained only in moderate yields by this process.

It is furthermore known that in the reaction of acid chlorides with substituted benzaldehydes and alkali metal cyanides, the yields of α-cyano-benzyl esters can be improved and the reaction times can be greatly shortened if the reactions are carried out in multi-phase systems consisting of a little water, if appropriate solid alkali metal cyanide and aprotic solvents, phase transfer catalysts being used if appropriate (see DE-OS (German Published No.) 2,708,590 and U.S. Pat. Nos. 4,110,360, 4,110,363 and 4,123,451).

It is also known from DE-OS (German Published Specification) 2,708,590 that α-phenyl-alkanecarboxylic acid esters can be obtained by reacting the corresponding acid chlorides, alkali metal cyanide and benzaldehydes in a two-phase solvent system if special reaction conditions, such as a certain ratio of the amount of water to that of cyanide, are applied. Alkenylcyclopropanecarboxylic acid α-cyanophenoxybenzyl esters, which are particularly interesting as pesticides, can be prepared in high yields with a short reaction time in this manner, according to DE-OS (German Published No.) 2,708,590, only by using phase-transfer catalysts.

The present invention now provides a process for the preparation of a substituted (cyclo)-alkanecarboxylic acid α-cyano-3-phenoxy-benzyl ester of the general formula

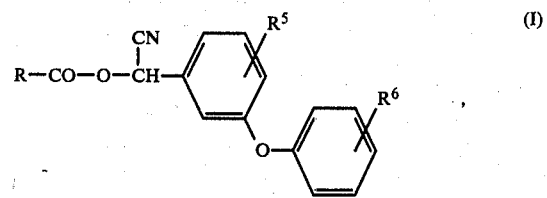

in which

R represents an open-chain or cyclic alkyl radical which optionally carries one or more substituents selected from halogen, alkyl, cycloalkyl, alkenyl (which is optionally substituted by halogen and/or alkoxy), styryl (which optionally carries one or more substituents selected from halogen and optionally halogen-substituted alkyl, alkoxy, alkylenedioxy and alkylthio radicals), spirocyclically linked, optionally halogen-substituted cycloalk(en)yl (which is optionally benzo-fused) and optionally substituted phenyl and $R^5$ and $R^6$ are identical or different and each represent hydrogen or halogen, in which an aqueous solution or suspension of at least an equimolar amount of a water-soluble cyanide is added to a mixture of a (cyclo)alkane-carboxylic acid chloride of the general formula

in which

R has the meaning indicated above, and a 3-phenoxybenzaldehyde of the general formula

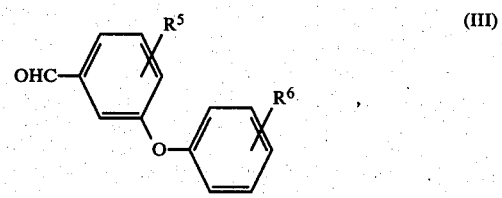

in which $R^5$ and $R^6$ have the meanings indicated above, in a solvent from the hydrocarbon series which is virtually immiscible with water, at a temperature between 0° and 80° C.

It is surprising, especially in view of the state of the art presented in DE-OS (German Published No.) 2,708,590, that substituted alkenylcyclopropanecarboxylic acid α-cyano-benzyl esters can be prepared in virtually quantitative yields in a short reaction time by the process according to the invention without using phase-transfer catalysts.

If, for example, 3-(2,2-dibromo-vinyl)-2,2-dimethyl-cyclopropane-1-carboxylic acid chloride and 3-phenoxy-4-fluoro-benzaldehyde are used as starting substances and an aqueous solution of sodium cyanide is used, in addition to hexane as the organic solvent, the reaction of these compounds can be outlined by the following equation:

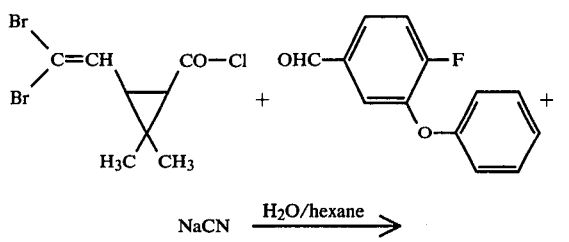

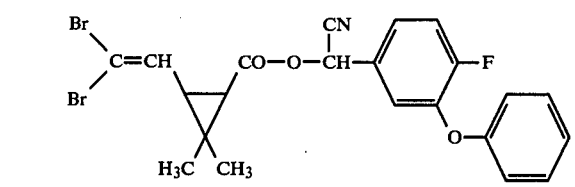

Formula (II) provides a definition of the (cyclo)-alkanecarboxylic acid chlorides to be used as starting compounds. Preferably, in this formula, R represents the radical

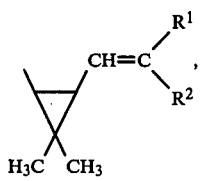

wherein $R^1$ represents hydrogen, methyl, fluorine, chlorine or bromine and $R^2$ represents methyl, fluorine, chlorine, bromine, $C_1$-$C_2$-fluoroalkyl or $C_1$-$C_2$-chlorofluoroalkyl, or represents phenyl which is optionally substituted by halogen and/or by an optionally halogen-substituted $C_1$-$C_4$-alkyl, $C_1$-$C_4$-alkoxy, $C_1$-$C_4$-alkylthio or $C_1$-$C_2$-alkylene-dioxy radical, or $R^1$ and $R^2$ together represent $C_2$-$C_5$-alkanediyl(alkylene), or R represents the radical

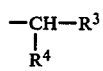

wherein $R^3$ represents phenyl which is optionally substituted by halogen and/or by an optionally halogen-substituted $C_1$-$C_4$-alkyl, $C_1$-$C_4$-alkoxy, $C_1$-$C_4$-alkylthio or $C_1$-$C_2$-alkylenedioxy radical and $R^4$ represents isopropyl or cyclopropyl, or R represents one of the radicals

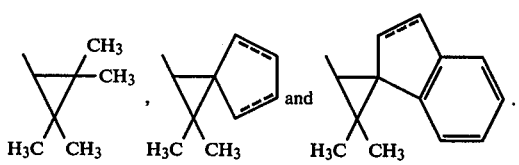

Preferably, in the benzaldehydes of the formula (III), $R^5$ and $R^6$ are identical or different and each represents hydrogen or fluorine.

Starting compounds of the formula (II) in which R represents the radical

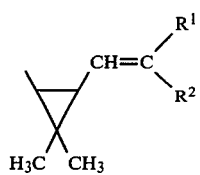

wherein $R^1$ and $R^2$ each represents fluorine, chlorine or bromine or wherein $R^1$ represents fluorine, chlorine or bromine and $R^2$ represents phenyl, 4-fluoro-phenyl or 4-chlorophenyl, are very particularly preferred.

Particularly preferably, in the benzaldehydes of the formula (III), $R^5$ represents fluorine and $R^6$ represents hydrogen.

Examples of the starting substances of the formula (II) which may be mentioned are: 3-(2,2-dichlorovinyl)-, 3-(2,2-dibromo-vinyl)-, 3-(2-chloro-2-phenylvinyl)-, 3-(2-chloro-2-(4-fluoro-phenyl)-vinyl)- and 3-(2-chloro-2-(4-chloro-phenyl)-vinyl)-2,2-dimethylcyclopropane-1-carboxylic acid chloride.

3-Phenoxy-4-fluoro-benzaldehyde may be mentioned as an example of the starting compounds of the formula (III).

The starting compounds of the formulae (II) and (III) are already known (see DE-OS's (German Published No.) 2,709,264 and 2,730,515, British Pat. No. 1,413,491 and 2,000,764 and U.S. Pat. No. 3,835,176 and 3,962,458).

Water-soluble cyanides which can be used in the process according to the invention are, for example, sodium cyanide and potassium cyanide; sodium cyanide is preferably used.

Water-immiscible solvents which are employed in the process according to the invention are preferably straight-chain or branched alkanes or cycloalkanes with 5 to 10 carbon atoms, for example n-pentane, n-hexane, n-heptane, n-octane, n-nonane, n-decane, 2-methylpentane, 3-methylpentane, 2-methylhexane, 2,2,4-trimethylpentane, cyclohexane or methylcyclohexane, or methylbenzenes, for example toluene or xylenes; mixtures of these hydrocarbons can also be used. Cyclohexane is the particularly preferred solvent component.

The reaction temperature is kept from about 0° to 80° C., preferably about 10° to 50° C. and especially about 15° to 35° C., in the process according to the invention.

The process is usually carried out under normal pressure.

In general, between 0.8 and 1.1 moles, preferably 0.9 to 1 mol, of 3-phenoxy-benzaldehyde, 1 to 2 mols, preferably 1.1 to 1.4 mols, of cyanide, 50 to 1,500 ml, preferably 100 to 1,000 ml, of water and 100 to 3,000 ml, preferably 200 to 2,000 ml, of the water-immiscible solvent are employed per mol of acid chloride of the formula (II).

The reaction time for a conversion of over 95% is in general between 1 and 5 hours.

In preferred embodiments of the present process, the starting compounds of the formulae (II) and (III) are dissolved in the water-immiscible solvent, and an aqueous solution of the cyanide is metered slowly into this solution, while stirring vigorously, the temperature of the reaction mixture being kept in the range indicated above by external cooling if appropriate. The entire mixture is stirred for a further one or more hours. For working up, if appropriate, the mixture is diluted with further water-immiscible solvent and the organic phase is separated off, washed with water, dried and filtered. The filtrate is freed from the solvent by distillation under reduced pressure, whereupon the product is obtained as an oily residue.

The 3-alkenyl-2,2-dimethyl-cyclopropane-1-carboxylic acid chlorides mentioned as preferred starting compounds of the formula (II) contain asymmetric carbon atoms and can exist in a corresponding number of stereo-isomeric forms, as can the corresponding products of the formula (I).

The configuration existing at the cyclopropane skeleton in the starting compounds is virtually completely retained in the process according to the invention.

The (cyclo)alkanecarboxylic acid α-cyano-3-phenoxybenzyl esters to be prepared by the process according to the invention can be used as agents for combating pests (see DE-OS (German Published Nos.) 2,709,264 and 2,730,515).

The active compounds are well tolerated by plants, have a favorable level of toxicity to warm-blooded animals, and can be used for combating arthropod pests, especially insects and acarids, which are encountered in agriculture, in forestry, in the protection of stored products and of materials, and in the hygiene field. They are active against normally sensitive and resistant species and against all or some stages of development. The above-mentioned pests include:

from the class of the Isopoda, for example *Oniscus asellus, Armadillidium vulgare* and *Porcellio scaber;* from the class of the Diplopoda, for example *Blaniulus guttulatus;* from the class of the Chilopoda, for example *Geophilus carpophagus* and Scutigera spec.;

from the class of the Symphyla, for example *Scutigerella immaculata;* from the order of the Thysanura, for example *Lepisma saccharina;* from the order of the Collembola, for example *Onychiurus armatus;* from the order of the Orthoptera, for example *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria;* from the order of the Dermaptera, for example *Forficula auricularia;* from the order of the Isoptera, for example Reticulitermes spp.;

from the order of the Anoplura, for example *Phylloxera vastatrix,* Pemphigus spp., *Pediculus humanus corporis,* Haematopinus spp. and Linognathus spp.;

from the order of the Mallophaga, for example Trichodectes spp. and Damalinea spp.;

from the order of the Thysanoptera, for example *Hercinothrips femoralis* and *Thrips tabaci;* from the order of the Heteroptera, for example Eurygaster spp., *Dysdercus intermedius, Piesma quadrata, Cimex lectularius, Rhodnius prolixus* and Triatoma spp.;

from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.;

from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Cacoecia podana, Capua reticulana, Choristoneura fumiferana, Clysia ambiguella, Homona magnanima* and *Tortrix viridana;* from the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica;* from the order of the Hymenoptera, for example Diprion spp., Hoplocampa spp., Lasius spp., *Monomorium pharaonis* and Vespa spp.;

from the order of the Diptera, for example Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa;* from the order of the Siphonaptera, for example *Xenopsylla cheopis* and Ceratophyllus spp.;

from the class of the Arachnida, for example *Scorpio maurus* and *Latrodectus mactans;* from the order of the Acarina, for example *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp..

The active compounds can be converted into the customary formulations, such as solutions, emulsions, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention may be used in the form of their formulations of the types that are commercially available or in the use forms prepared from these formulations.

The active compound content of the use forms prepared from the formulations of the types that are commercially available can vary within wide ranges. The active compound concentration of the use forms can be from 0.0000001 to 100% by weight of active compound, preferably from 0.0001 to 10% by weight.

The compounds may be employed in a customary manner appropriate for the particular use forms.

When used against pests harmful to health and pests of stored products, the active compounds are distinguished by an excellent residual activity on wood and clay as well as a good stability to alkali on limed substrates.

The compounds may also be employed to combat ectoparasites, especially ticks, that infest domesticated animals, for example sheep or cattle.

In the veterinary field, the active compounds according to the invention may be used in a known manner, such as orally in the form of, for example, tablets, capsules, drenches and granules; dermally by means of, for example, dipping, spraying, pouring-on, spotting-on and powdering; and parenterally, for example by means of injections. They may also be used by the so-called "feed-through" process.

The present invention also provides an arthropodicidal composition containing as active ingredient a compound of the present invention in admixture with a solid or liquefied gaseous diluent or carrier or in admixture with a liquid diluent or carrier containing a surface-active agent.

The present invention also provides a method of combating arthropods (especially insects or acarids) which comprises applying to the arthropods, or to a habitat thereof, a compound of the present invention alone or in the form of a composition containing as active ingredient a compound of the present invention in admixture with a diluent or carrier.

The present invention also provides a method of freeing or protecting domesticated animals from ectoparasitical insects or acarids (especially ticks) which comprises applying to said animals a compound according to the present invention, in admixture with a diluent or carrier.

The present invention further provides crops protected from damage by arthropods by being grown in areas in which immediately prior to and/or during the time of the growing a compound of the present invention was applied alone or in admixture with a diluent or carrier.

It will be seen that the usual methods of providing a harvested crop may be improved by the present invention.

The present invention further provides domesticated animals whenever freed or protected from ectoparasitical insects or acarids by the application to said animals of a compound according to the present invention, in admixture with a diluent or carrier.

PREPARATIVE EXAMPLE

A solution of sodium cyanide in water was added dropwise to a solution of 45 mmol of 3-phenoxy-4-fluorobenzaldehyde and 50 mmol of an acid chloride of the formula (II) in cyclohexane, while stirring vigorously and cooling with ice. The mixture was stirred at 25° C. for three hours. It was then diluted with cyclohexane and the organic phase was separated off, washed with water, dried over sodium sulphate and filtered. The solvent was carefully distilled off from the filtrate.

The various amounts of the reaction components employed and the yields are found in the following table:

TABLE

(balance sheet of amounts)

| acid chloride | NaCN (mmol) | cyclohexane (ml) | water | Yield (% of theory) |
|---|---|---|---|---|
| 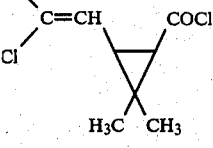 | 65 | 10 | 7 | 94.5 |
| 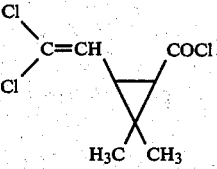 | 60 | 100 | 5 | 95 |
| 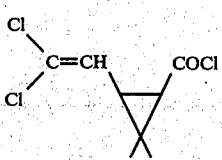 | 60 | 50 | 20 | 97 |
| 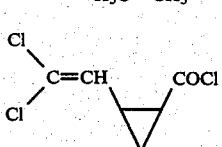 | 60 | 50 | 50 | 97 |
| 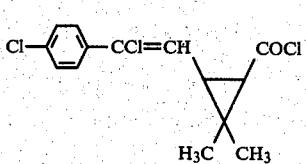 | 60 | 100 | 5 | 86 |
| 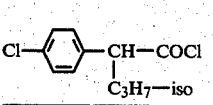 | 60 | 100 | 5 | 99 |

It will be appreciated that the instant specification and examples are set forth by way of illustration and not limitation, and that various modifications and changes may be made without departing from the spirit and scope of the present invention.

We claim:

1. A process for the preparation of a substituted (cyclo)alkanecarboxylic acid α-cyano-3-phenoxy-benzyl ester of the formula

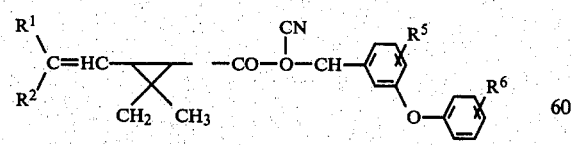

in which
$R^1$ is hydrogen, methyl, fluorine, chlorine or bromine and
$R^2$ is methyl, fluorine, chlorine, bromine, $C_1$-$C_2$-fluoroalkyl or $C_1$-$C_2$-chlorofluoroalkyl, phenyl, phenyl substituted by halogen and/or by an optionally halogen-substituted $C_1$-$C_4$-alkyl, $C_1$-$C_4$-alkoxy, $C_1$-$C_4$-alkylthio or $C_1$-$C_2$-alkylenedioxy radical, or
$R^1$ and $R^2$ together are $C_2$-$C_5$-alkanediyl, comprising adding an aqueous solution or suspension of at least an equimolar amount of a water-soluble cyanide to a mixture of an alkanecarboxylic acid chloride of the formula R—CO—Cl and a 3-phenoxy-benzaldehyde of the formula

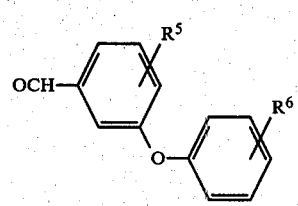

in a hydrocarbon solvent which is virtually immiscible with water at a temperature between about 0° and 80° C.

2. A process according to claim 1, in which
R$^1$ is fluorine, chlorine or bromine, and
R$^2$ is fluorine, chlorine, bromine, phenyl, 4-fluorophenyl or 4-chloro-phenyl.

3. A process according to claim 1, in which the 3-phenoxybenzaldehyde is 3-phenoxy-4-fluoro-benzaldehyde.

4. A process according to claim 1, in which the water-soluble cyanide is sodium cyanide or potassium cyanide.

5. A process according to claim 1, in which the water-immiscible solvent is selected from the group consisting of alkanes and cycloalkanes with 5 to 10 carbon atoms, methyl-substituted benzenes and mixtures thereof.

6. A process according to claim 5, wherein the solvent is selected from the group consisting of n-pentane, n-hexane, n-heptane, n-octane, n-nonane, n-decane, 2-methylpentane, 3-methylpentane, 2-methylhexane, 2,2,4-trimethylpentane, cyclohexane, methylcyclohexane, toluene, xylenes, and mixtures thereof.

7. A process according to claim 1, wherein the reaction is effected between about 10° and 50° C.

8. A process according to claim 1, wherein the reaction is effected between about 15° and 35° C.

9. A process according to claim 1, wherein between about 0.8 and 1.1 mols of the 3-phenoxy-benzaldehyde, about 1 to 2 mols of the cyanide, about 50 to 1,500 ml of water and about 100 to 3,000 ml of the water-immiscible solvent are employed per mol of the acid chloride.

10. A process according to claim 1, wherein about 0.9 to 1 mol of the 3-phenoxy-benzaldehyde, about 1.1 to 1.4 mols of the cyanide, about 100 to 1,000 ml of water and about 200 to 2,000 ml of water-immiscible solvent are employed per mol of the acid chloride.

11. A process according to claim 2, wherein the 3-phenoxybenzaldehyde is 3-phenoxy-4-fluoro-benzaldehyde, the water soluble cyanide is sodium cyanide or potassium cyanide, the solvent is selected from the group consisting of n-pentane, n-hexane, n-heptane, n-octane, n-nonane, n-decane, 2-methylpentane, 3-methylpentane, 2-methylhexane, 2,2,4-trimethylpentane, cyclohexane, methylcyclohexane, toluene, xylenes, and mixtures thereof, the reaction is effected between about 15° and 35° C., and about 0.9 to 1 mol of the 3-phenoxy-benzaldehyde, about 1.1 to 1.4 mols of the cyanide, about 100 to 1,000 ml of water and about 200 to 2,000 ml of water-immiscible solvent are employed per mol of the acid chloride.

* * * * *

UNITED STATES PATENT AND TRADEMARK OFFICE
CERTIFICATE OF CORRECTION

PATENT NO. : 4,350,640
DATED : September 21, 1982
INVENTOR(S) : Rainer Fuchs et al Page 1 of 2

It is certified that error appears in the above—identified patent and that said Letters Patent is hereby corrected as shown below:

Col. 9, line 60    Middle of Structure, delete

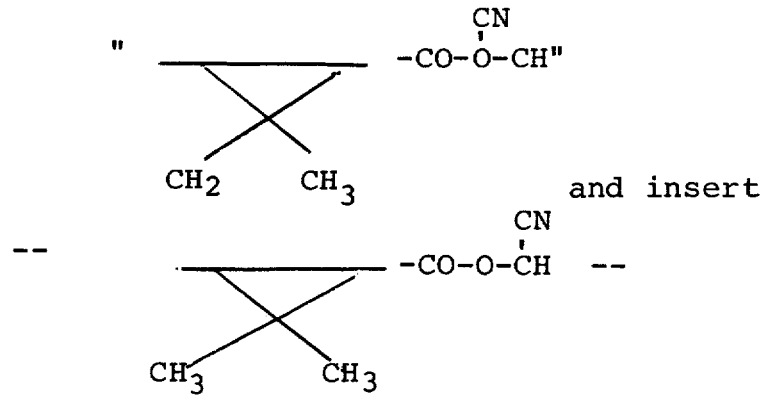

and insert

UNITED STATES PATENT AND TRADEMARK OFFICE
CERTIFICATE OF CORRECTION

PATENT NO. : 4,350,640  
DATED : September 21, 1982  
INVENTOR(S) : Rainer Fuchs et al Page 2 of 2

It is certified that error appears in the above—identified patent and that said Letters Patent is hereby corrected as shown below:

Col. 10, line 56        Delete "R-CO-Cl" and insert

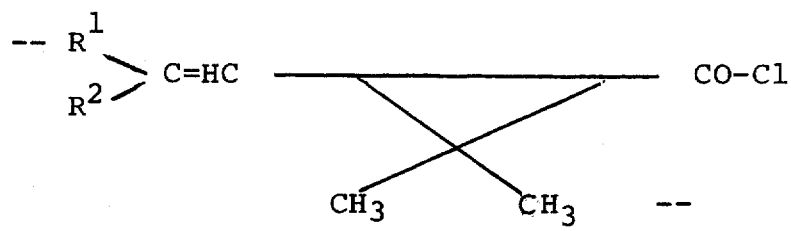

Signed and Sealed this

Seventh Day of December 1982

[SEAL]

Attest:

GERALD J. MOSSINGHOFF

Attesting Officer    Commissioner of Patents and Trademarks